(12) United States Patent
Pierce et al.

(10) Patent No.: US 8,708,944 B2
(45) Date of Patent: Apr. 29, 2014

(54) SYSTEM FOR HARVESTING AND DISPENSING A FIBRIN CLOT

(76) Inventors: Javin C. Pierce, Stowe, VT (US); Peter Kurzweil, Newport Coast, CA (US)

( * ) Notice: Subject to any disclaimer, the term of this patent is extended or adjusted under 35 U.S.C. 154(b) by 399 days.

(21) Appl. No.: 12/749,282

(22) Filed: Mar. 29, 2010

(65) Prior Publication Data

US 2011/0034851 A1    Feb. 10, 2011

Related U.S. Application Data

(63) Continuation-in-part of application No. 12/714,047, filed on Feb. 26, 2010, now abandoned.

(60) Provisional application No. 61/155,842, filed on Feb. 26, 2009, provisional application No. 61/164,212, filed on Mar. 27, 2009.

(51) Int. Cl.
*A61K 31/195*    (2006.01)

(52) U.S. Cl.
USPC .......................................... 604/6.01; 606/214

(58) Field of Classification Search
None
See application file for complete search history.

(56) References Cited

U.S. PATENT DOCUMENTS

| | | |
|---|---|---|
| 3,153,496 A | 10/1964 | Johnson |
| 3,828,987 A | 8/1974 | Drummond et al. |
| 4,646,738 A | 3/1987 | Trott |
| 4,674,500 A | 6/1987 | DeSatnick |
| 4,790,819 A | 12/1988 | Li et al. |
| 5,118,428 A | 6/1992 | Sand et al. |
| 2003/0069601 A1 * | 4/2003 | Nowakowski et al. ....... 606/214 |
| 2004/0037819 A1 | 2/2004 | Pascher et al. |
| 2006/0243676 A1 | 11/2006 | Swift et al. |
| 2009/0236297 A1 | 9/2009 | Dorian et al. |

OTHER PUBLICATIONS

Arnoczky, S.P., et al., Meniscal Repair Using an Exogenous Fibrin Clot—An Experimental Study in Dogs, The Journal of Bone and Joint Surgery, 1988, pp. 1209-1217.

Henning, C.E., et al., Vascularity for Healing of Meniscus Repairs, Arthroscopy: The Journal of Arthroscopic and Related Surgery, 1987, pp. 13-18, vol. 3, No. 1, Raven Press.

* cited by examiner

*Primary Examiner* — Leslie Deak
*Assistant Examiner* — Sara Sass
(74) *Attorney, Agent, or Firm* — Pandiscio & Pandiscio

(57) ABSTRACT

A system for harvesting a fibrin clot and depositing that fibrin clot into a wound site during a surgical procedure, the system comprising:
  (i) blood drawing apparatus for drawing blood;
  (ii) extraction apparatus for extracting fibrin from blood so as to form a fibrin clot;
  (iii) configuring apparatus for molding, cutting and shaping the fibrin clot into a desired configuration; and
  (iv) dispensing apparatus for reliably and controllably dispensing the fibrin clot at a selected location in the body.

8 Claims, 13 Drawing Sheets

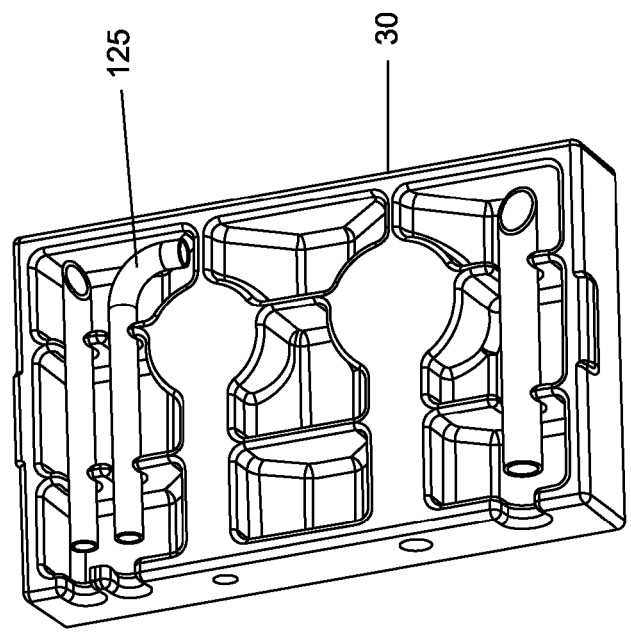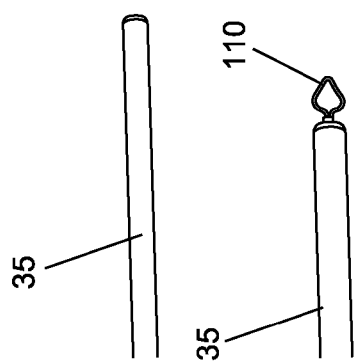
FIG. 20

US 8,708,944 B2

SYSTEM FOR HARVESTING AND DISPENSING A FIBRIN CLOT

REFERENCE TO PENDING PRIOR PATENT APPLICATIONS

This patent application:

(1) is a continuation-in-part of prior U.S. patent application Ser. No. 12/714,047, filed Feb. 26, 2010 now abandoned by Javin C. Pierce et al. for SYSTEM FOR HARVESTING AND DISPENSING BLOOD CLOT, which patent application in turn claims benefit of prior U.S. Provisional Patent Application Ser. No. 61/155,842, filed Feb. 26, 2009 by Javin C. Pierce et al. for SYSTEM FOR HARVESTING AND DISPENSING BLOOD CLOT; and (2) claims benefit of pending prior U.S. Provisional Patent Application Ser. No. 61/164,212, filed Mar. 27, 2009 by Javin C. Pierce et al. for SYSTEM FOR HARVESTING AND DISPENSING BLOOD CLOT.

The three (3) above-identified patent applications are hereby incorporated herein by reference.

FIELD OF THE INVENTION

This invention relates to surgical methods and apparatus in general, and more particularly to a novel method and apparatus for harvesting a fibrin clot and depositing that fibrin clot into a wound site during a surgical procedure.

BACKGROUND OF THE INVENTION

The creation of a hematoma or fibrin clot is an initial and important phase in wound repair. The fibrin clot provides a matrix scaffold as well as a chemotactic stimulus to the various cellular elements involved in wound repair. The fibrin clot is typically a naturally-occurring response to an injury to vascularized tissue.

However, this fibrin clotting is frequently absent in injuries to certain types of tissue which are not highly vascularized, e.g., the meniscus of the knee. Clinical and experimental observations have shown, however, that in many cases the insertion of a fibrin clot into the point of injury in such tissue will aid in the healing process. Furthermore, it has also been found that the insertion of a fibrin clot into other settings (e.g., the point of attachment of a graft ligament to a host bone) can also enhance the speed and integrity of the ligament attachment process.

In practice, it can be time consuming and inconvenient to harvest a fibrin clot and deposit that fibrin clot into a wound site during a surgical procedure.

Thus there is a need for a new and improved method and apparatus for harvesting a fibrin clot and depositing that fibrin clot into a wound site during a surgical procedure.

SUMMARY OF THE INVENTION

The present invention provides a new and improved method and apparatus for harvesting a fibrin clot and depositing that fibrin clot into a wound site during a surgical procedure.

In one preferred form of the invention, there is provided a system for harvesting a fibrin clot and depositing that fibrin clot into a wound site during a surgical procedure, the system comprising:

(i) blood drawing apparatus for drawing blood;
(ii) extraction apparatus for extracting fibrin from blood so as to form a fibrin clot;
(iii) configuring apparatus for molding, cutting and shaping the fibrin clot into a desired configuration; and
(iv) dispensing apparatus for reliably and controllably dispensing the fibrin clot at a selected location in the body.

In another preferred form of the invention, there is provided a system for harvesting a fibrin clot and depositing that fibrin clot into a wound site during a surgical procedure, the system comprising:

(i) blood drawing apparatus for drawing blood;
(ii) extraction apparatus for extracting fibrin from blood so as to form a fibrin clot;
(iii) a flat surface for holding the fibrin clot;
(iv) configuring apparatus for molding, cutting and shaping the fibrin clot into a desired configuration; and
(v) dispensing apparatus for reliably and controllably dispensing the fibrin clot at a selected location in the body.

In another preferred form of the invention, there is provided a method for harvesting a fibrin clot and depositing that fibrin clot at a wound site during a surgical procedure, the method comprising:

drawing blood from a patient;
extracting fibrin from blood so as to form a fibrin clot;
reconfiguring the fibrin clot into a desired configuration; and
dispensing the fibrin clot at the wound site.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 20 is a schematic view showing a kit for harvesting and dispensing fibrin clot.

DETAILED DESCRIPTION OF THE PREFERRED EMBODIMENTS

Coring Tube System

In one preferred embodiment of the present invention, there is provided a novel system for harvesting and dispensing a fibrin clot, wherein the novel system comprises (i) means to draw blood; (ii) means to extract fibrin from the blood so as to form a fibrin clot; (iii) means for molding, cutting and shaping the fibrin clot into a desired configuration; and (iv) means for reliably and controllably dispensing the fibrin clot at a selected location in the body, whereby to facilitate healing.

Figure 1:
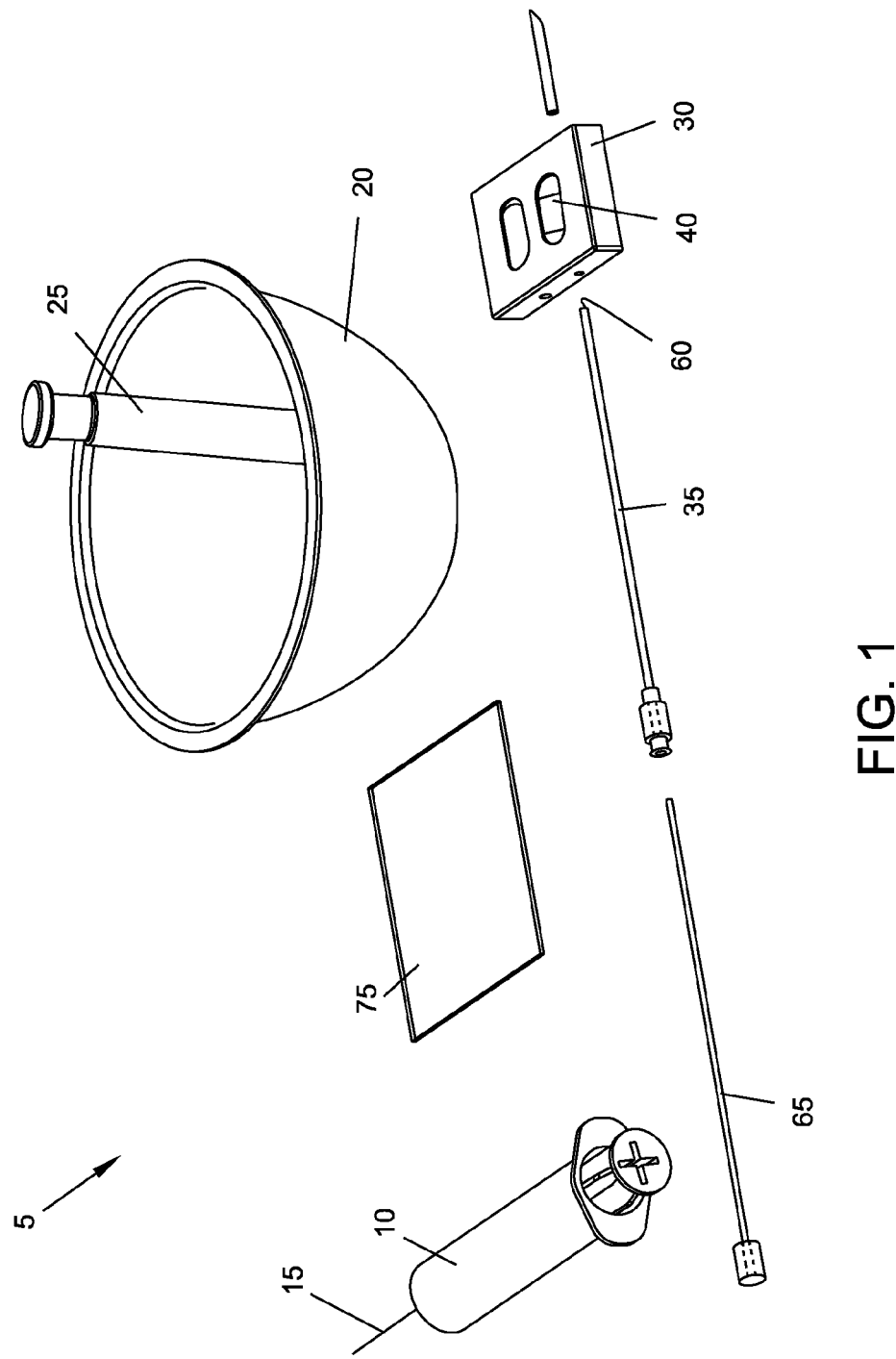
FIG. 1 is a schematic view showing a system for harvesting and dispensing a fibrin clot.

More particularly, and looking now at FIG. 1, there is shown a novel system 5 for harvesting and dispensing a fibrin clot.

Novel system 5 comprises means to draw blood, preferably in the form of a conventional blood-drawing syringe 10 including a conventional blood-drawing needle 15. If desired, the blood can be drawn from the patient who is to receive the fibrin clot (in which case the fibrin clot created from that blood may be referred to as a fibrin clot) or, alternatively, the blood can be drawn from another donor (in which case the fibrin clot created from that blood may be referred to as an exogenous fibrin clot).

Novel system 5 also comprises means to extract fibrin from the blood so as to form a fibrin clot, preferably in the form of a bowl or vessel 20 for holding the drawn blood, and a frosted glass rod 25 for stirring (i.e., agitating) the drawn blood held in bowl 20 for a period of time until a fibrin clot forms. Thus it will be seen that frosted glass rod 25 generally acts as a precipitator for the fibrin clot. If desired, frosted glass rod 25 can be replaced by another implement which is configured to precipitate fibrin clot, e.g., a metal member with a highly disrupted surface (such as a scratched surface, a holed surface, a screened surface, etc.).

Novel system 5 also comprises means for molding, cutting and shaping the fibrin clot into a desired configuration, preferably in the form of a clot preparation block 30 for receiving and holding the fibrin clot and a coring tube 35 for excising and storing a plug of cored fibrin clot.

Figure 2:
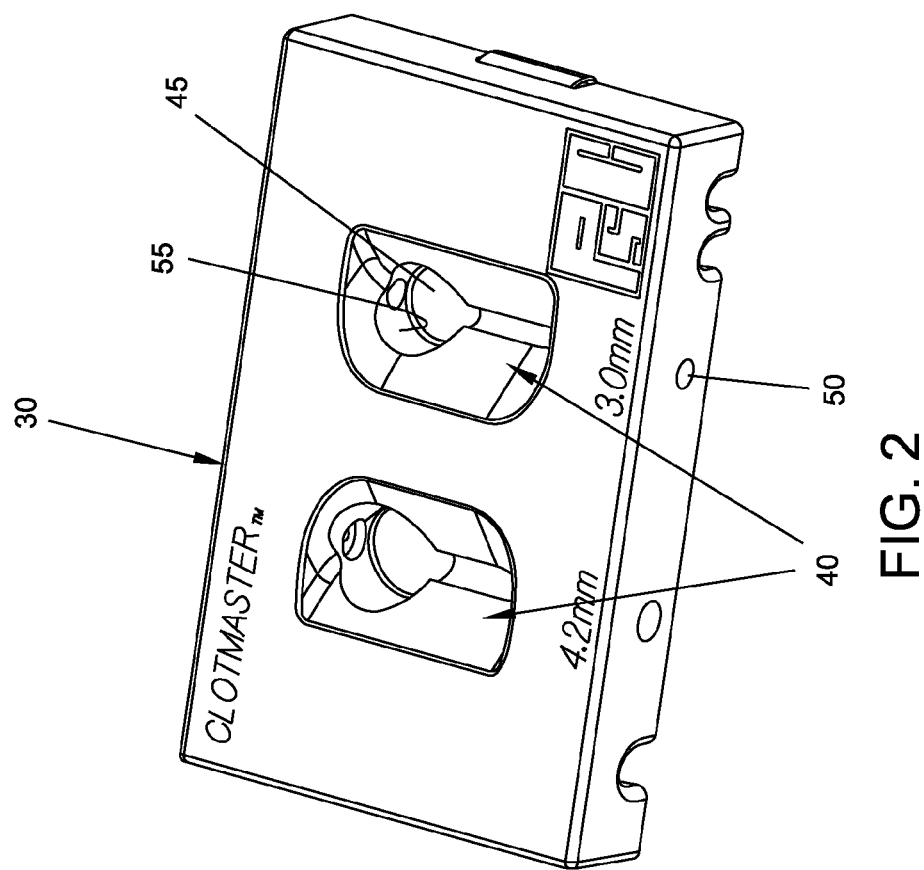
FIG. 2 is a schematic view showing further details of the clot preparation block of the system shown in FIG. 1.

More particularly, and as seen in FIGS. 1 and 2, clot preparation block 30 preferably comprises at least one chamber 40 generally in the form of a funneled hopper and having a coring well 45 disposed at its bottom end. A bore 50 extends through clot preparation block 30 and communicates with chamber 40. A stop face 55 is disposed in chamber 40, diametrically opposed to bore 50. Coring tube 35 preferably comprises a relatively sharp distal rim 60. On account of the foregoing construction, and as will hereinafter be discussed in further detail, when a fibrin clot is disposed in chamber 40 of clot preparation block 30, and coring tube 35 is thereafter advanced through bore 50, across chamber 40, and against stop face 55, coring tube 35 will core out a plug of the fibrin clot and store the cored fibrin clot within the lumen of coring tube 35. If desired, coring tube 35 may be passed through chamber 40 just once so as to core out a plug of the fibrin clot and store that plug within the interior of coring tube 35. Alternatively, coring tube 35 may be passed through chamber 40 multiple times, preferably with the fibrin clot being repacked within chamber 40 between passes of the coring tube, so as to core out a plurality of cored fibrin clots and store those plugs within coring tube 35.

Novel system 5 also comprises means for reliably and controllably dispensing the cored fibrin clot at a selected location in the body, preferably in the form of a plunger 65 which is passed through the lumen of coring tube 35 so as to expel the cored fibrin clot into the body. The length of plunger 65 is preferably slightly longer than the length of coring tube 35, so that when the plunger is completely inserted within the coring tube, the tip of the plunger extends beyond the end of the coring tube, whereby to ensure that the cored fibrin clot is completely ejected from the coring tube and that no material sticks or clings to the end of the coring tube. Plunger 65 can be mounted in coring tube 35 either before or after the coring tube has been used to core plugs of fibrin clot from chamber 40. In one preferred form of the invention, plunger 65 is inserted into coring tube 35 after the coring tube has cored out a plug of the fibrin clot and while the coring tube is still in engagement with stop face 55, so as to cause plunger 65 to closely "pack" the cored out morsels of fibrin clot within the coring tube. Furthermore, in one preferred form of the invention, plunger 65 includes graduated markings on its shaft so that the amount of fibrin clot stored in coring tube 35 and/or expelled from coring tube 35 can be measured.

System 5 may be used in the following manner to harvest a fibrin clot and deposit that fibrin clot into a wound site:

1. Blood is drawn from the patient using syringe 10 and needle 15 (FIG. 1).

Figure 3:
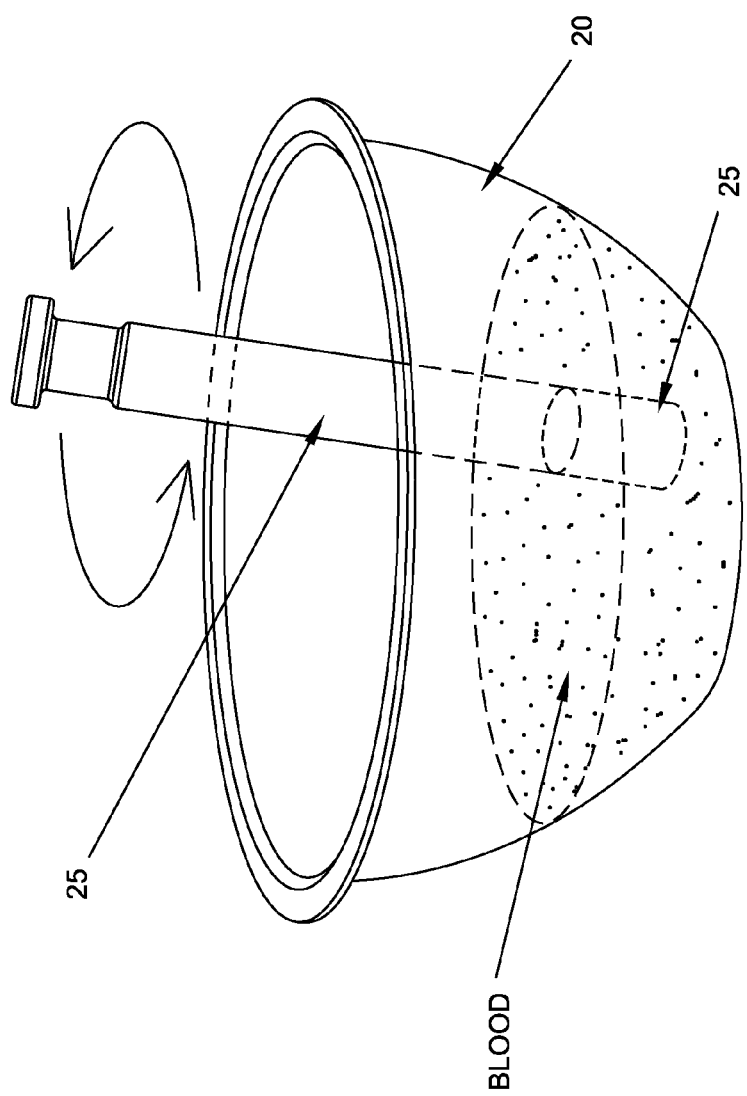
FIG. 3 is a schematic view showing drawn blood being stirred in a vessel so as to precipitate fibrin clot.

2. The blood is transferred from syringe 10 to bowl 20 (FIG. 3).

Figure 4:
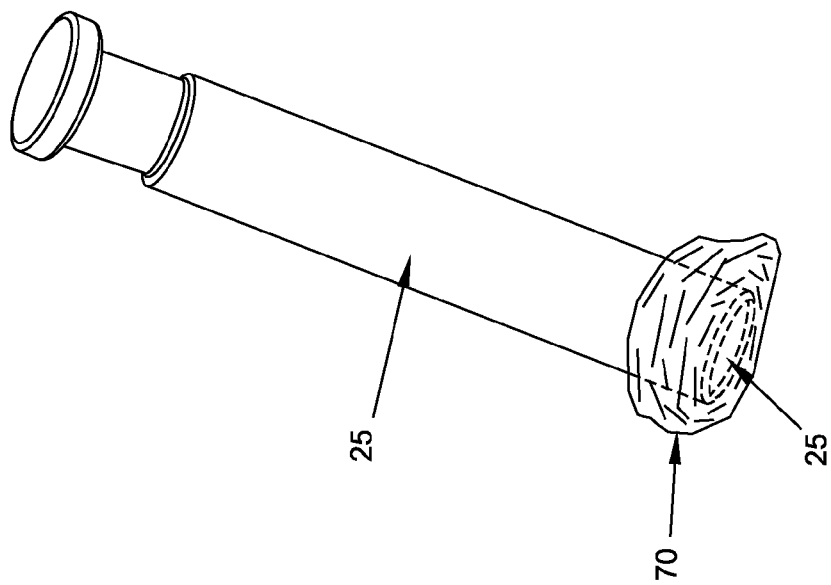
FIG. 4 is a schematic view showing fibrin clot precipitated on a frosted glass rod.

3. Once the blood is in bowl 20, the blood is stirred with frosted glass rod 25 until fibrin clot 70 precipitates on frosted glass rod 25 (FIG. 4).

4. The fibrin clot 70 is removed from frosted glass rod 25, e.g., with gauze 75 (FIG. 1), preferably blotting off excess liquid.

Figure 5:
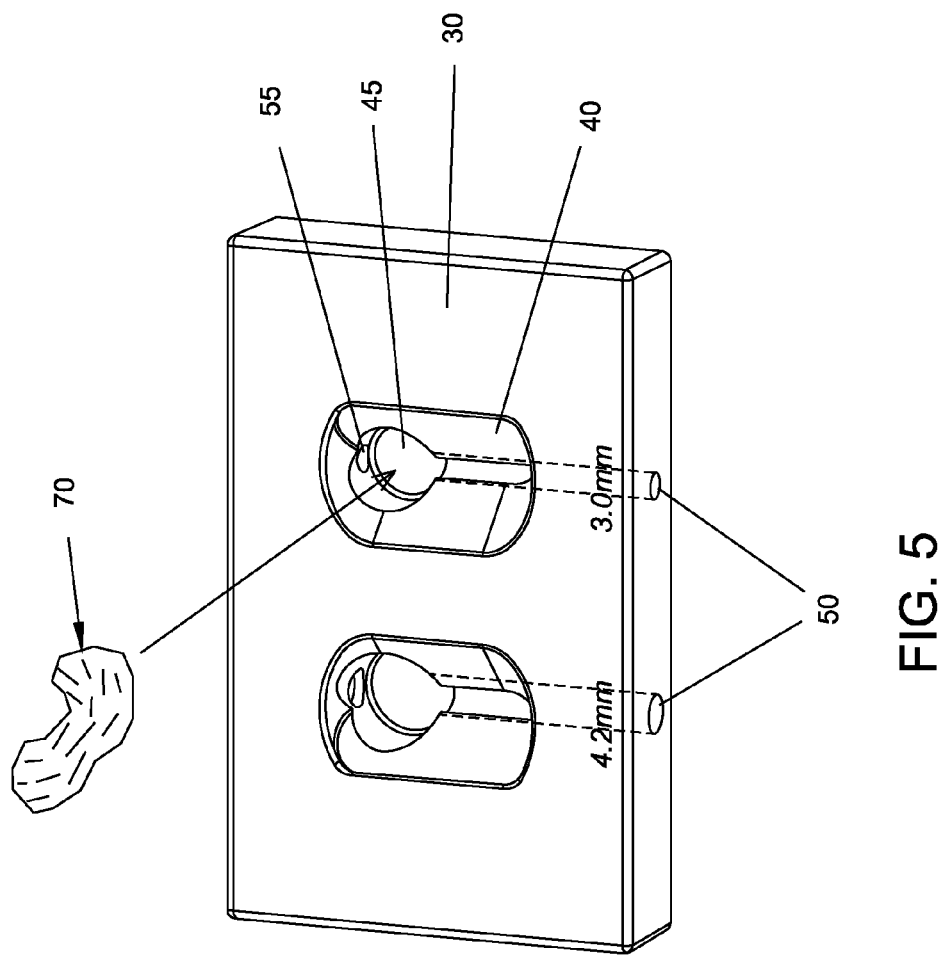
FIG. 5 is a schematic view showing a fibrin clot being deposited in the clot preparation block.

5. The fibrin clot 70 is placed into chamber 40 of clot preparation block 30 (FIG. 5).

6. The fibrin blood clot 70 is forced deep into chamber 40 and into coring well 45 at the base of the chamber, e.g., using gauze 75.

Figure 6:
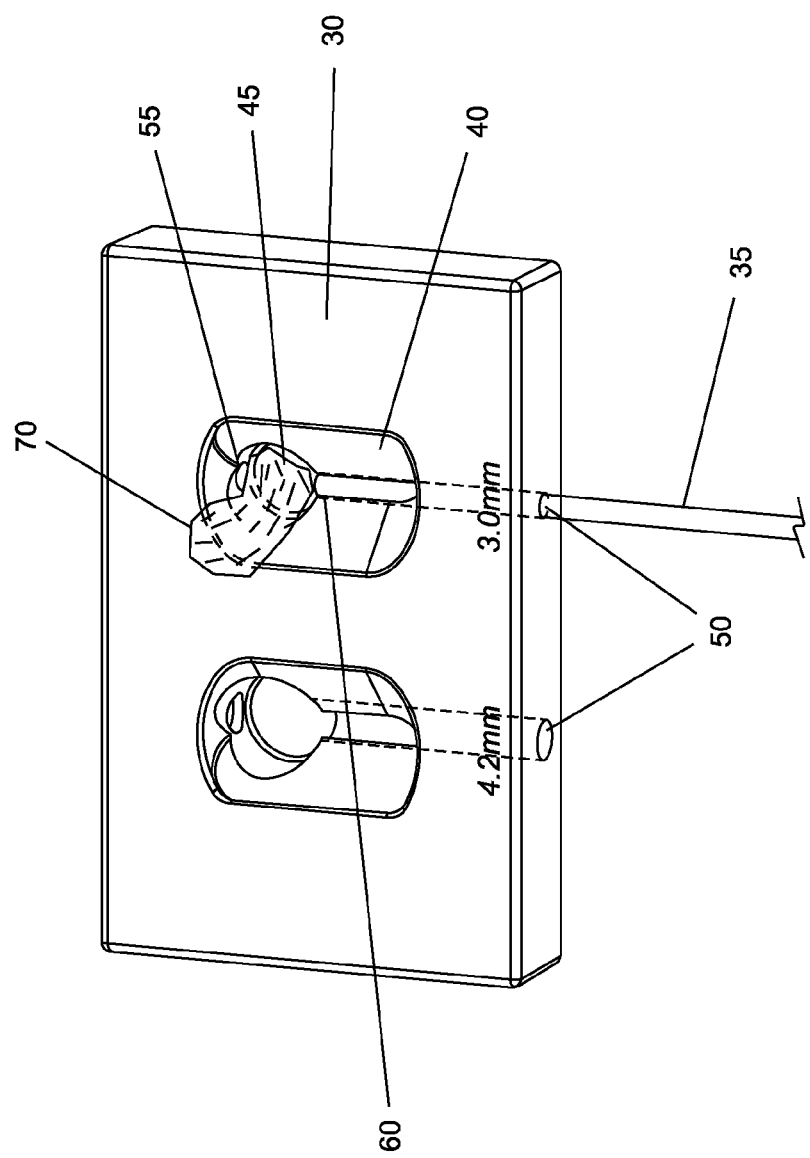
FIG. 6 is a schematic view showing a coring tube being advanced into engagement with the fibrin clot.
Figure 7:
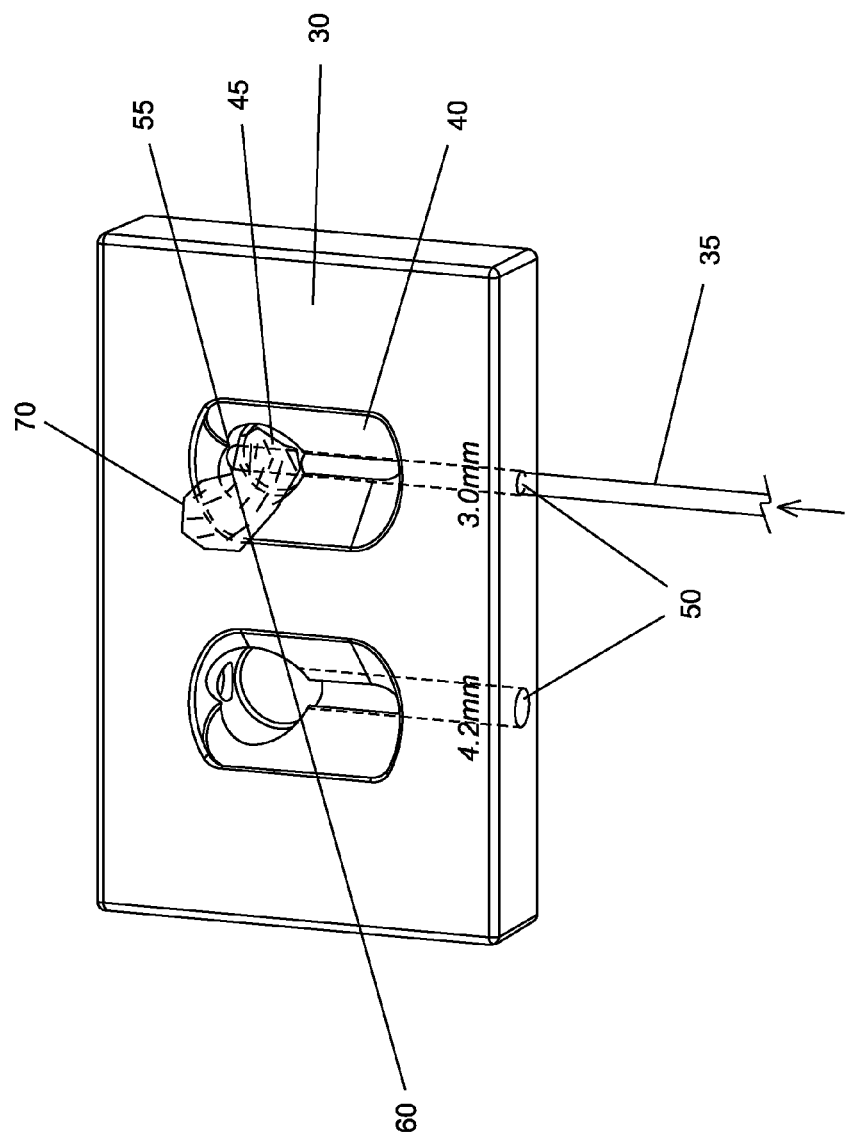
FIG. 7 is a schematic view showing the coring tube coring the fibrin clot while the fibrin clot is disposed in the clot preparation block.

7. Coring tube 35 is advanced through bore 50 of clot preparation block 30 until the distal end of coring tube 35 passes through coring well 45, coring the fibrin clot 70 as it goes (FIGS. 6 and 7). Forward movement of coring tube 35 preferably continues until the distal end of coring tube 35 engages stop face 55 of clot preparation block 30.

Figure 8:
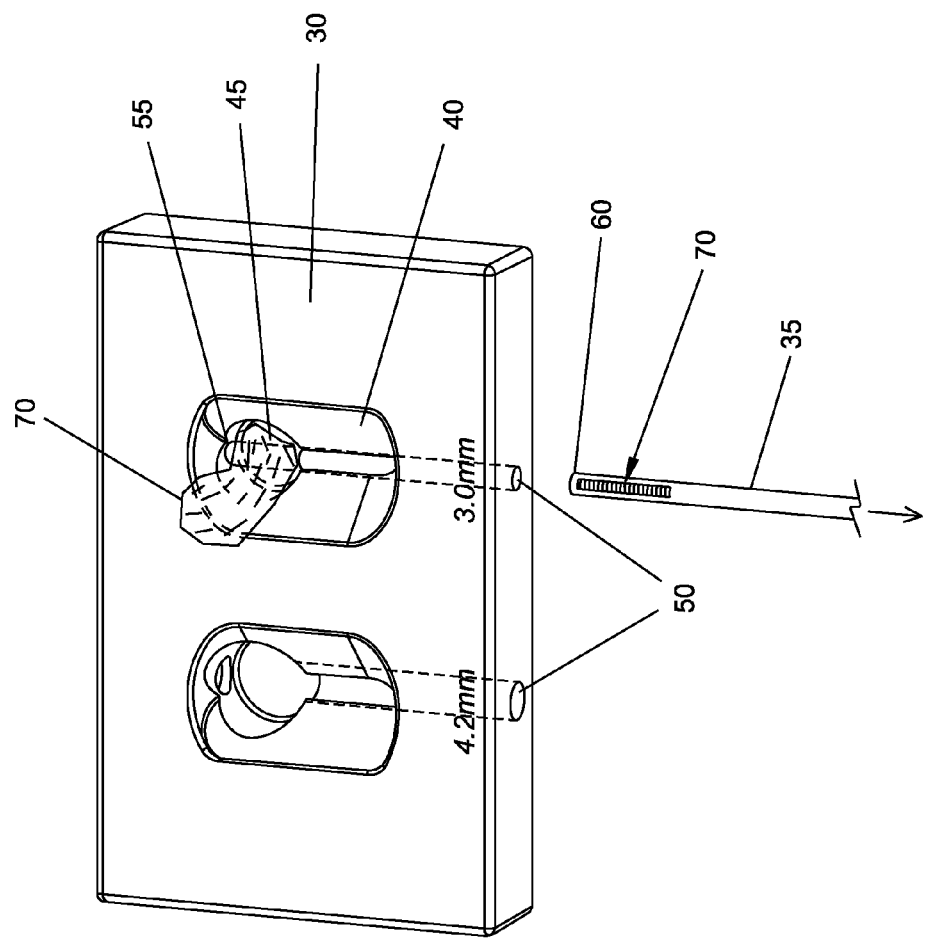
FIG. 8 is a schematic view showing the coring tube retracting from the clot preparation block, carrying cored fibrin clot with it.
Figure 9:
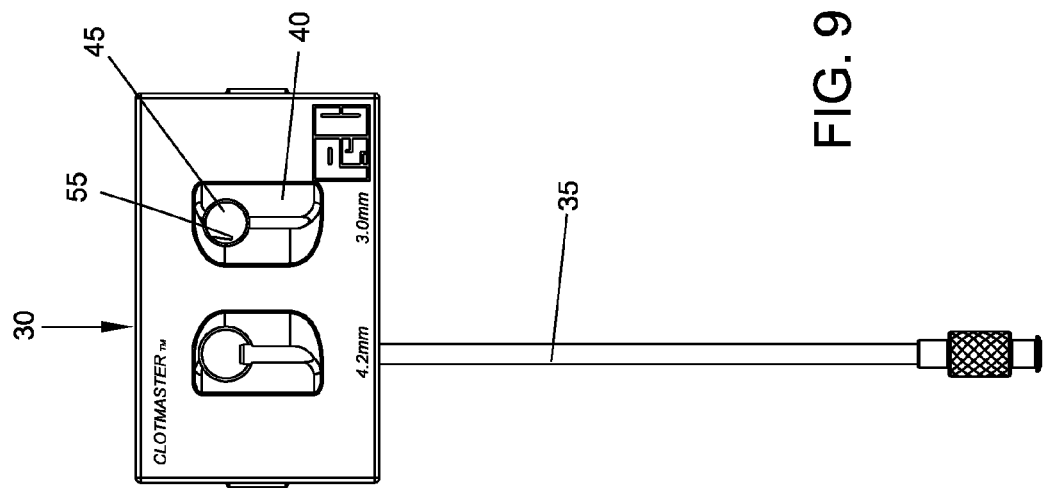
FIG. 9 is a schematic view showing a coring tube disposed in a clot preparation block.
Figure 10:
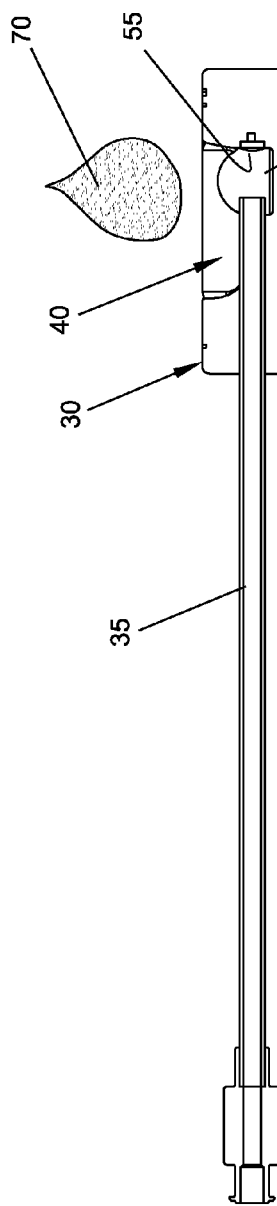
FIGS. 10-12 show how suction may be used to draw fibrin clot into the coring tube.
Figure 11:
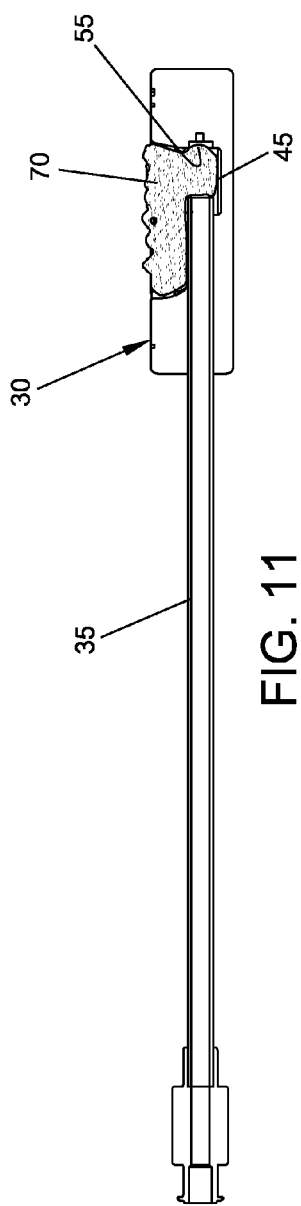
Figure 12:
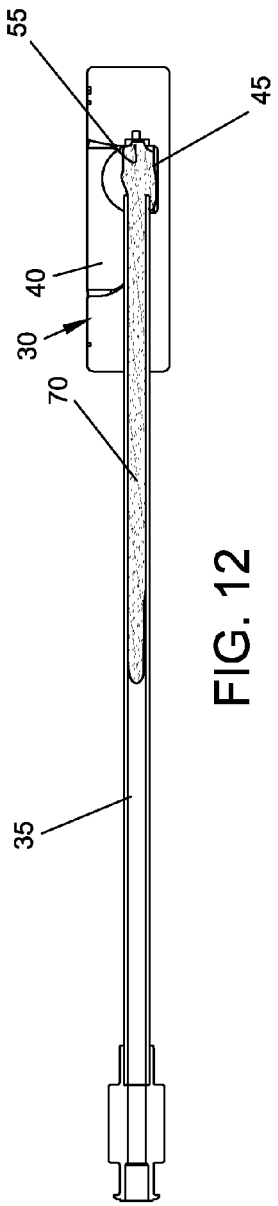

8. With coring tube 35 engaging stop face 55, the coring tube is twisted back and forth so as to further core the fibrin clot, whereby to store a plug of fibrin clot within the interior of coring tube 35. If desired, plunger 65 can have been inserted in the lumen of coring tube 35 as the coring tube cores the fibrin clot, in which case the plunger will back out of the coring tube as the coring tube fills with the plug of fibrin clot, thereby providing a visual indication of the amount of fibrin clot stored in coring tube 35. Coring tube 35 is then withdrawn from clot preparation block 30 (FIG. 8).

9. If it is desired to increase the amount of fibrin clot stored in coring tube 35, the fibrin clot in chamber 40 can be pressed back down into coring well 45, and then Steps 7 and 8 above repeated so as to increase the amount of fibrin clot stored in coring tube 35.

10. When the desired amount of fibrin clot 70 has been captured in the lumen of coring tube 35, the coring tube and its associated plunger 65 are inserted into the body adjacent to the wound site where the fibrin clot is to be deployed.

11. The distal tip of coring tube 35 is advanced through the body until it is disposed adjacent to the site where the fibrin clot is to be deployed (which may include passing the distal tip of the coring tube through intervening tissue), and then plunger 65 is advanced distally so as to expel the fibrin clot into the tissue.

Significantly, since the fibrin clot comprises an elongated cylindrical structure within the coring tube, ejection of the fibrin clot from the coring tube can involve delivery of a plurality of separate "beads" of fibrin clot at separate locations at the wound site, or the delivery of an elongated "continuous bead" of fibrin clot material at the wound site.

Vacuum System

In the foregoing description, mechanical engagement of coring tube 35 with stop face 55 is used to core a segment of the fibrin clot into the interior of the coring tube. However, other arrangements are also possible.

For one thing, suction can be applied to the proximal end of coring tube 35 so as to draw a segment of the fibrin clot into the interior of the tube, with the cored segment of the fibrin clot separating from the remainder of the fibrin clot mass as the suction overcomes the integrity of the fibrin clot mass. See FIGS. 9-12.

Furthermore, in the foregoing description, plunger 65 is used to expel the cored fibrin clot from the coring tube. However, if desired, pressure can be applied to the proximal end of the coring tube so as to expel the cored fibrin clot from the interior of the coring tube.

Suture System

It is also possible to mount the cored fibrin clot onto a suture so that the suture can be used to manipulate the cored fibrin clot, whereby to facilitate its placement at the surgical site. Among other things, the cored fibrin clot can be run down the suture so as to facilitate deployment of the cored fibrin clot. This feature can be extremely useful in situations where a suture anchor may be deployed in bone and the suture emanating from the suture anchor used to "tie down" soft tissue (e.g., a ligament) to the bone. In such a situation, mounting the cored fibrin clot onto the suture provides a fast and simple way to ensure that the fibrin clot is deployed at the location where the suture emanates from the bone, i.e., at the precise location where the soft tissue is to be reattached to the bone.

Figure 13:
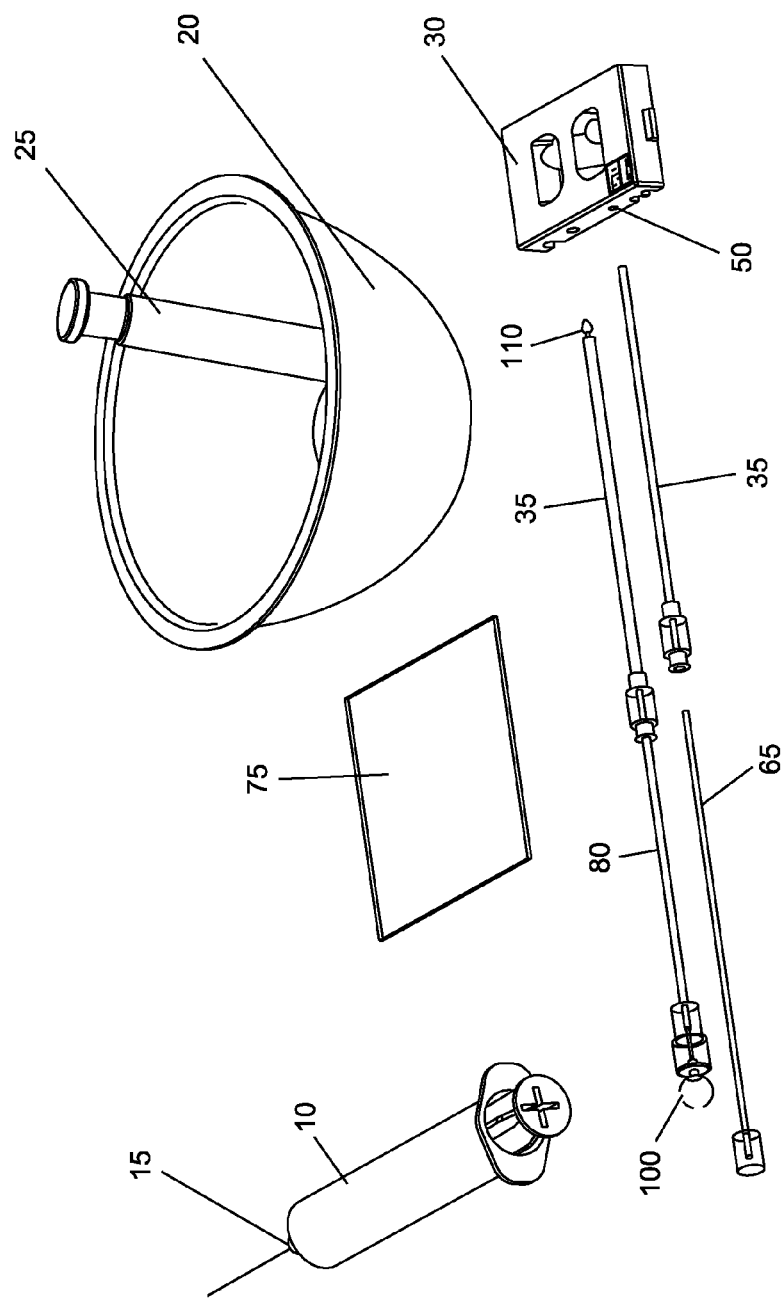
FIG. 13 is a schematic view showing an alterative system for harvesting and dispensing a fibrin clot.
Figure 14:
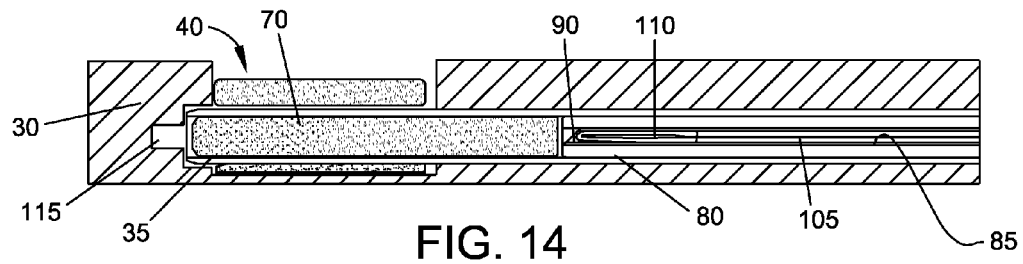
FIGS. 14-19 are schematic views showing how the system of FIG. 13 may be used to harvest and dispense fibrin clot.
Figure 15:
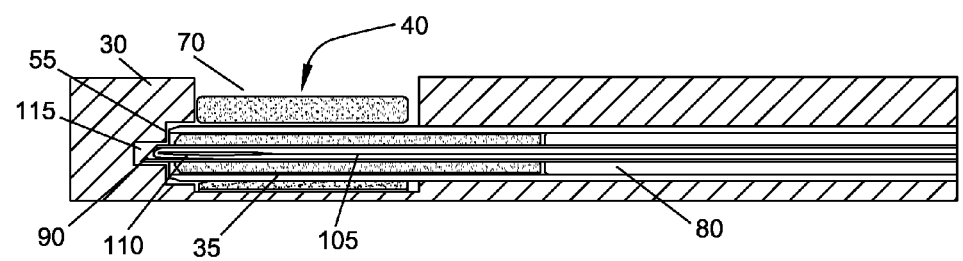
Figure 16:
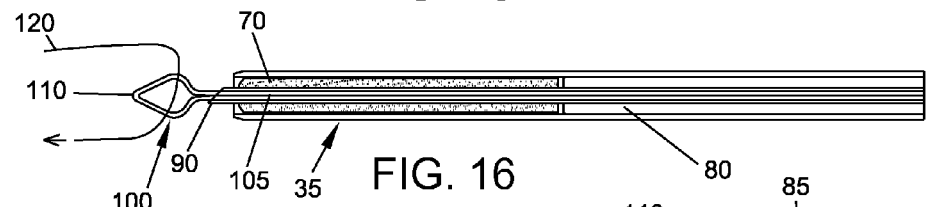
Figure 17:
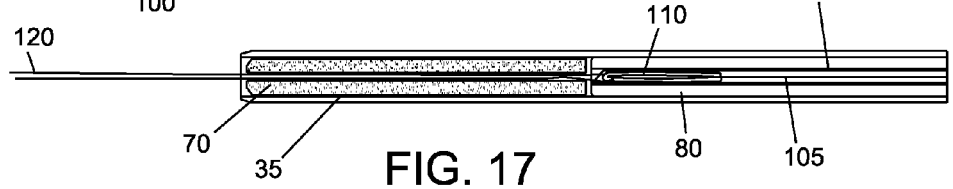
Figure 18:
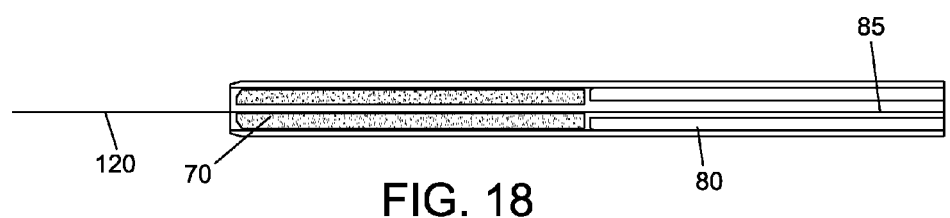
Figure 19:
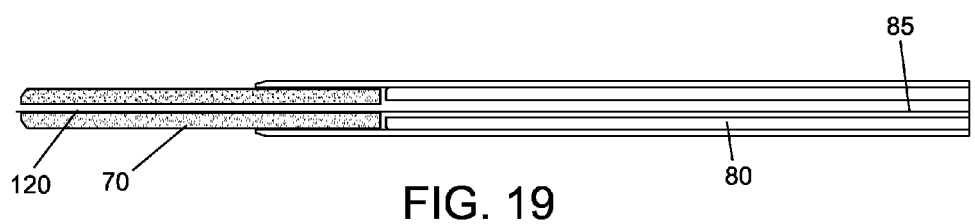

More particularly, in this alternative form of the invention, and looking now at FIG. 13, there is provided the aforementioned coring tube 35, a modified plunger 80 having a lumen 85 (FIG. 14) extending therethrough, a sharp passer tube 90, and a suture retriever 100 comprising a shaft 105 having a suture pickup loop 110 at its distal end (FIG. 16). In this form of the invention, and looking now at FIG. 14, after fibrin clot 70 has been disposed in chamber 40 in clot preparation block 30, and after coring tube 35 has been passed through the mass of the fibrin clot 70, sharp passer tube 90 is passed through plunger 80 and coring tube 35 until the distal end of the sharp passer tube passes through fibrin clot 70 and enters a recess 115 formed in stop face 55. As this occurs, fibrin clot 70 is prevented from extruding from coring tube 35 by stop face 55 (FIG. 15). Then coring tube 35 is retracted from clot preparation block 30, with the distal tip of sharp passer tube 90 standing proud of the end of coring tube 35 and fibrin clot 70. Next, suture retriever 100 is passed down sharp passer tube 90 so that suture pickup loop 110 extends out the distal end of sharp passer tube 90 (FIG. 16). Then suture 120 is loaded into suture pickup loop 110, and suture retriever 100 is retracted back through sharp passer tube 90 so as to pull suture 120 through fibrin clot 70 (FIG. 17). Thereafter, when the cored fibrin clot is to be deployed in the body, suture 120 is held taut outside of the body (FIG. 18), plunger 80 is moved distally so as to expel fibrin clot 70 from coring tube 35 (FIG. 19). As noted above, suture 120 may be the suture emanating from a bone anchor deployed in bone, in which case mounting the cored fibrin clot onto the suture provides a fast and simple way to ensure that the fibrin clot is deployed at the location where the suture emanates from the bone, i.e., at the precise location where the soft tissue is to be reattached to the bone. Alternatively, suture 120 may be suture from another source.

Alternatively, if desired, suture 120 can be omitted, and sharp passer tube 90 can be used as a sort of retractable skewer to hold the fibrin clot impaled thereon, and to subsequently help manipulate the fibrin clot after it is ejected from the coring tube. The skewer (i.e., sharp passer tube 90) can be retracted against plunger 80 to help strip impaled fibrin clots from the skewer.

Thus it will be seen that the present invention provides means to safely apply suture to fibrin clot 70 without the risk of needle stick injuries, by providing a clot preparation block which includes a chamber for receiving the fibrin clot and a protective backstop for cutting clot morsels with the sharp coring tube and for protected needle passing for drawing the suture through the fibrin clot. Alternately, suction can be applied to the coring tube so as to load the coring tube with liquid or flowable gel clot from the chamber. The coring tube and plunger provide means to contain and control the clot-suture construct while introducing the clot-suture construct into the body, and means to release the clot from the coring tube, and means to run the fibrin clot down the suture to the repair site so that the clot can closely approximate the defect site. Furthermore, the suture can be used to secure the fibrin clot to adjacent tissue at the repair site.

The invention also comprises means to eject fibrin clot at an angle to the longitudinal axis of the coring tube, by providing a curved tip 125 (FIG. 20) for the coring tube, or by means of a malleable central wire or shaft upon which the fibrin clot may be impaled.

The surgical method includes the steps of performing arthroscopic surgery on a knee, hip or elbow joint, or other joint, by placing a number of small incisions in the skin adjacent to the area of the joint. Viewing apparatus, which may preferably be an arthroscope, is positioned into the joint. The physician inserts a number of cutting and suctioning tools into the wound site to repair the damage seen therein. Thereafter, the coring tube of the present invention, which has been filled with a pre-determined amount of fibrin clot and has its plunger partially inserted therein, is inserted into the joint. The physician, while viewing the operation through an arthroscope, manipulates the coring tube and its plunger, preferably with one hand, so as to eject the cored fibrin clot into the wound or damaged tissue site where needed. The physician can determine the amount of fibrin clot ejected by visualizing the graduated marks located on the shaft of the plunger, or by watching the relationship between the plunger handle and the proximal end of coring tube. If suture is threaded though the fibrin clot, the physician can hold the suture taut and run the applicator assembly down the suture to the repair site. In one form of the invention, the suture threaded through the fibrin clot in the coring tube emanates from soft or hard tissue or from a suture anchor disposed at the surgical site. The physician then removes the applicator device and stitches the wound site closed to complete the operation and allow the joint to heal.

"Cookie Cutter" Construction

In yet another form of the invention, the fibrin clot gathered on the precipitator (e.g., frosted glass rod 25) is deposited on a flat surface, and then coring tube 35 is pressed down against the fibrin clot deposited on the flat surface so as to core the fibrin clot using the rim of the coring tube, in a cookie cutter sort of fashion. This action cores plugs of fibrin clot from the large flat sheet of fibrin clot, and loads those plugs into the interior of the coring tube. If desired, the fibrin clot may be dried and/or compressed prior to such coring.

In another form of the invention, a fibrin clot having an amorphous shape is deposited in a recess comprising a flat surface which acts as a "cutting board" for the distal end of the coring tube and parallel or angled sides which serve to centralize the clot mass into the path of the coring tube, thereby increasing the size of the plugs.

Modifications

It will be understood that many changes in the details, materials, steps and arrangements of parts, which have been herein described and illustrated in order to explain the nature of the invention, may be made by those skilled in the art without departing from the principles and scope of the present invention

What is claimed is:

1. A method for harvesting a fibrin clot and depositing that fibrin clot at a wound site during a surgical procedure, the method comprising:
   drawing blood from a patient;
   extracting fibrin from blood so as to form a fibrin clot;
   reconfiguring the fibrin clot into a desired configuration; and
   dispensing the fibrin clot at the wound site;
   wherein extracting fibrin from blood so as to form a fibrin clot is effected using a metal bowl and a frosted glass rod.

2. A method according to claim 1 wherein reconfiguring the fibrin clot into a desired configuration is effected using a clot preparation block including a chamber for receiving fibrin clot, and a coring tube for coring the fibrin clot while it is seated in the chamber.

3. A method according to claim 2 wherein dispensing the fibrin clot at the wound site is effected using a plunger which is moved through the coring tube.

4. A method according to claim 1 wherein reconfiguring the fibrin clot into a desired configuration is effected using a clot preparation block including a chamber for receiving fibrin clot, and a coring tube for coring the fibrin clot while it is seated in the chamber, with suction being applied to the coring tube so as to draw the fibrin clot into the interior of the coring tube.

5. A method according to claim 4 wherein dispensing the fibrin clot at the wound site is effected by applying pressure to the coring tube.

6. A method according to claim 1 wherein a suture is passed through the fibrin clot prior to dispensing the fibrin clot at the wound site.

7. A method according to claim 6 wherein dispensing the fibrin clot at the wound site is effected by running the fibrin clot down the suture.

8. A method according to claim 1 wherein the wound site comprises at least one the group consisting of a bone, a tendon and a muscle.

* * * * *